United States Patent
Rittig et al.

(10) Patent No.: US 10,316,106 B2
(45) Date of Patent: *Jun. 11, 2019

(54) METHOD FOR PROCESSING CELLULOSE-CONTAINING BIOMASS

(71) Applicant: BASF SE, Ludwigshafen (DE)

(72) Inventors: Frank Rittig, Worms (DE); Stefan Koch, Mainz (DE); Alois Kindler, Gruenstadt (DE); Michael Koch, Speyer (DE); Ferdinand Leifeld, Ludwigshafen (DE); Vaidotas Navickas, Mannheim (DE); Markus Gruen, Birkenheide (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/552,521

(22) PCT Filed: Feb. 18, 2016

(86) PCT No.: PCT/EP2016/053417
§ 371 (c)(1),
(2) Date: Aug. 22, 2017

(87) PCT Pub. No.: WO2016/135030
PCT Pub. Date: Sep. 1, 2016

(65) Prior Publication Data
US 2018/0044438 A1 Feb. 15, 2018

(30) Foreign Application Priority Data
Feb. 23, 2015 (EP) .................................... 15156141

(51) Int. Cl.
| | | |
|---|---|---|
| *C12P 19/14* | (2006.01) | |
| *C12P 7/10* | (2006.01) | |
| *C08B 15/02* | (2006.01) | |
| *C12N 1/10* | (2006.01) | |
| *C08B 1/00* | (2006.01) | |
| *C08H 8/00* | (2010.01) | |
| *C12P 19/02* | (2006.01) | |
| *C13K 1/02* | (2006.01) | |

(52) U.S. Cl.
CPC .............. *C08B 1/003* (2013.01); *C08B 15/02* (2013.01); *C08H 8/00* (2013.01); *C12P 19/02* (2013.01); *C13K 1/02* (2013.01); *Y02E 50/16* (2013.01)

(58) Field of Classification Search
CPC ......... C12P 19/02; C08B 1/003; C08B 15/02; C12K 1/02; C08H 8/00
USPC .................................... 435/99, 483; 424/486
See application file for complete search history.

(56) References Cited

U.S. PATENT DOCUMENTS

2012/0029247 A1    2/2012    Holbrey et al.

FOREIGN PATENT DOCUMENTS

| EP | 0 472 474 A1 | 2/1992 |
| EP | 2 033 974 A1 | 3/2009 |
| WO | WO 2004/081185 A2 | 9/2004 |
| WO | WO 2008/134037 A1 | 11/2008 |
| WO | WO 2015/049345 A1 | 4/2015 |

OTHER PUBLICATIONS

Extended European Search Report dated Jul. 20, 2015 in Patent Application No. 15156141.2.
International Search Report and Written Opinion of the International Searching Authority dated May 13, 2016 in Patent Application No. PCT/EP2016/053417.
Yangiao Jin, et al., "Liquefaction of Lignin by Polyethyleneglycol and Glycerol" Bioresource Technology, vol. 102, No. 3, XP055151326, Feb. 1, 2011, pp. 3581-3583.
Rajeev Kumar, et al., "Effect of Additives on the Digestibility of Corn Stover Solids Following Pretreatment by Leading Technologies" Biotechnology and Bioengineering, vol. 102, No. 6, XP055079510, Apr. 15, 2009, pp. 1544-1557.
Mareike Monschein, et al., "Dissecting the Effect of Chemical Additives on the Enzymatic Hydrolysis of Pretreated Wheat Straw" Bioresource Technology, vol. 169, XP055196639, Jul. 21, 2014, pp. 713-722.
Hairong Zhang, et al., "Acid-Catalyzed Liquefaction of Bagasse in the Presence of Polyhydric Alcohol" Applied Biochemistry and Biotechnology, vol. 170, No. 7, XP055196984, Aug. 1, 2013, pp. 1780-1791.

*Primary Examiner* — Robert B Mondesi
*Assistant Examiner* — Mohammad Y Meah
(74) *Attorney, Agent, or Firm* — Oblon, McClelland, Maier & Neustadt, L.L.P.

(57) ABSTRACT

Described is a method for processing cellulose-containing biomass with sulfuric acid and certain additives, especially for the pretreatment of cellulose-containing biomass prior to saccharification.

18 Claims, No Drawings

METHOD FOR PROCESSING CELLULOSE-CONTAINING BIOMASS

Sugars generated from cellulose-containing biomass may be used as a feedstock for production of fuels, plastics, and other products. Due to the finite nature and instability of fossil feedstock supply and for environmental reasons, replacement of fossil feedstock by non-fossil feedstock, i.e. feedstock obtained from renewable resources, becomes more and more important. One potential source of such non-fossil feedstock is cellulose-containing biomass, which can be processed by enzymatic saccharification of cellulose to glucose which can be further processed into a plurality of products either chemically or by fermentation. For instance, by fermentation of the obtained glucose, ethanol (sometimes referred to as bio-ethanol) is obtainable which can be used as fuel for internal combustion engines, e.g. for cars.

In order to facilitate enzymatic saccharification, cellulose-containing biomass is usually subjected to a pretreatment in order to increase the accessibility of the cellulose biomass by degradation or decomposition of hemicellulose and/or lignin present in the cellulose-containing biomass. Several pretreatment processes are known in the art.

WO 2008/134037 discloses a method for digesting a lignocellulosic biomass, comprising treating a lignocellulosic biomass with a surfactant and optionally an acid (e.g. sulfuric acid) and incubating the surfactant treated lignocellulosic biomass with an enzyme. Preferred surfactants are chosen from the group consisting of Tween-80, Tween-20, PEG (molar mass not specified), DDBSA, glucopone/215, glucopone/225 and glucopone/625. WO 2004/081185 discloses a method for hydrolyzing lignocellulose, comprising contacting said lignocellulose with at least one chemical under moderate conditions to generate a treated lignocellulose, and contacting said treated lignocellulose with at least one enzyme capable of hydrolyzing lignocellulose, wherein said chemical is selected from the group consisting of oxidizing agents, denaturants, detergents, organic solvents, bases, and combinations thereof. In this regard, by "detergent" is intended a compound that can form micelles to sequester oils. Said detergents include anionic, cationic, and neutral detergents, including, but not limited to, Nonidet (N) P-40, sodium dodecyl sulfate (SDS), sulfobetaine, noctylglucoside, deoxycholate, Triton X-100, and Tween 20.

In the publication Bioresource Technology 169 (2014) 713-722 the ability of additives selected from the group consisting of polyethylene glycol PEG 8000, (polyethylene glycol having a molar mass of approximately 8000 g/mol), PEG 2000 (polyethylene glycol having a molar mass of approximately 2000 g/mol), Triton-X, Tween 20, Tween-80, cetyltrimethylammonium bromide (CTAB) and urea to increase the enzymatic hydrolysis of thermo-acidically pretreated wheat straw by *Trichoderma reesei* cellulase at 50° C. is studied. Herein, the additive is added to a suspension of thermo-acidically pretreated wheat straw. Presence of an additive during the thermo-acidical pretreatment is not disclosed.

Related art is also Rajeev Kumar et al., Biotechnology and Bioengineering, vol. 102, no. 6, 15 Apr. 2009, pages 1544-1557; EP 0 472 474 A1; Hairong Zhang et al., Applied Biochemistry and Biotechnology, vol. 170, no. 7, 1 Aug. 2013, pages 1780-1791; Yanqiao Jin et al., Bioresource Technology vol. 102 no. 3, 1 Feb. 2011, pages 3581-3583; EP 2 033 974 A1 and WO 2015/049345 A1.

WO 2008/134037 and WO 2004/081185 broadly disclose generic classes of additives for the pretreatment of cellulose-containing biomass prior to saccharification. However it has been found that the chemical structure as well as the molecule size of such additive has a strong influence on the effect of said additive. Surprisingly it has been found that the use of compounds of formula (I) as defined hereinbelow for processing cellulose-containing biomass, especially for the pretreatment of cellulose-containing biomass prior to saccharification, has an advantageous effect on the yield of glucose obtainable by enzymatic saccharification of the treated cellulose containing biomass and allows for a reduction of the enzyme dosage.

These and other objects are achieved by the method for processing cellulose-containing biomass according to the present invention. Said method for processing cellulose-containing biomass comprises the step of subjecting a treatment mixture comprising said cellulose-containing biomass, water and sulfuric acid
to a temperature in the range of from 100° C. to 220° C. at a pressure in the range of from 100 to 4000 kPa wherein the pressure is selected so that at least a part of the water is in the liquid state
to generate a treated cellulose-containing biomass,
wherein said treatment mixture further comprises one or more compounds of formula (I)

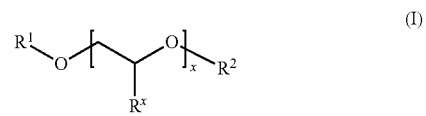

wherein in formula (I)
$R^1$ and $R^2$ are independently selected from the group consisting of hydrogen, methyl, ethyl, propyl and butyl,
each $R^x$ in any of said x groups (II)

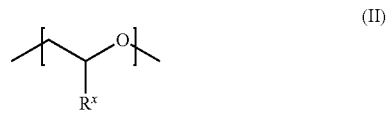

is independently of the meaning of $R^x$ in the other groups (II) selected from the group consisting of hydrogen, methyl, ethyl and propyl
x is an integer from 50 to 250.

The step of subjecting a treatment mixture as defined above comprising said cellulose-containing biomass, water, sulfuric acid and one or more compounds of formula (I) to a temperature in the range of from 100° C. to 220° C. at a pressure in the range of from 100 kPa to 4000 kPa wherein the pressure is selected so that at least a part of the water is in the liquid state facilitates saccharification, either enzymatic or chemical saccharification, of the obtained treated cellulose-containing biomass. Therefore, in a preferred method according to the present invention, said step provides a useful pretreatment of cellulose-containing biomass for saccharification, either enzymatic or chemical saccharification, or for the production of dissolving pulp.

The treated cellulose-containing biomass typically comprises cellulose, hemicellulose and lignin as major components. In contrast to the cellulose-containing biomass before processing, in the treated cellulose-containing biomass the content of hemicellulose and/or lignin is typically decreased due to decomposition to xylose and other degradation products which may include minor amounts of glucose. Accordingly, in a preferred method of the present invention, the composition of the treatment mixture and the temperature and pressure to which said treatment mixture is subjected are selected such as to decrease the amount of hemicellulose and/or lignin in the cellulose-containing biomass.

Without wishing to be bound to any specific theory, it is presently assumed that the compounds of formula (I) bind to lignin constituents of the cellulose-containing biomass thus preventing lignin from inhibiting the activity of the enzymes in enzymatic saccharification of the treated cellulose-containing biomass. Furthermore the compounds of formula (I) may facilitate swelling of the cellulose-containing biomass, resulting in stabilization of an open structure of the cellulose-containing biomass which improves the access of sulfuric acid as well as of enzymes for subsequent enzymatic saccharification. More specifically the molecules of the compounds of formula (I) may fill voids in the treated biomass which are formed due to decomposition of hemicellulose and/or lignin, thus avoiding densification and collapsing of the treated cellulose-containing biomass so that in the enzymatic saccharification access of enzymes is facilitated.

A further aspect of the present invention relates to the use of a compound of formula (I) as defined above for processing cellulose-containing biomass, especially for the pretreatment of cellulose-containing biomass prior to saccharification.

Treatment Mixture

The treatment mixture comprises a solid phase comprising cellulose containing biomass and a liquid aqueous phase comprising water, sulfuric acid and one or more compounds of formula (I).

Cellulose-containing biomass which is suitable for processing by the method of the present invention may be selected from the group consisting of plant biomass, agricultural wastes, forestry residues, sugar processing residues, paper waste and blends thereof. For economical and ecological reasons, cellulose containing biomass in the form of wastes and residues is especially preferably. Beside cellulose, cellulose-containing biomass typically comprises lignin and/or hemicellulose.

Preferably said treatment mixture comprises 3 wt.-% to 75 wt.-%, more preferably 8 wt.-% to 70 wt.-%, further preferably 15 wt.-% to 60 wt.-%, most preferably 25 wt.-% to 50 wt.-%, particularly preferably 30 wt.-% to 45 wt.-% of cellulose containing biomass, in each case based on the total weight of said treatment mixture. With a lower concentration of cellulose-containing biomass in the treatment mixture, the method becomes inefficient, because a very large volume of treatment mixture is handled for obtaining a small amount of treated cellulose-containing biomass. With a higher concentration of biomass in the treatment mixture, there is an issue that not all of the cellulose-containing biomass is in contact with the sulfuric acid and the one or more compounds of formula (I) as defined above.

Preferably the concentration of sulfuric acid in said treatment mixture is in the range of from 0.1 wt.-% to 25 wt.-%, more preferably 0.5 wt.-% to 10 wt.-%, most preferably 1 wt.-% to 5 wt.-% in each case based on the total weight of the cellulose-containing biomass present in the treatment mixture.

At a concentration below 0.1 wt.-% based on the total weight of the cellulose-containing biomass present in the treatment mixture, the amount of sulfuric acid in the treatment mixture is generally too low so that the sulfuric acid has no significant effect on the yield of glucose in subsequent saccharification. On the other hand, the higher the concentration of sulfuric acid in the treatment mixture, the higher is the amount of undesirable by-products. Sulfuric acid may act as an oxidation agent and/or as a dehydrating agent, therefore undesired by-products may be formed by coking and/or sulfatization of biomass constituents. Formation of such by-products in turn results in reduction of the amount of material available for saccharification, contamination of the reaction mixture, deactivation of enzymes used for saccharification, contamination of the reaction equipment (i.e. by formation of insoluble deposits) and difficulties in separating the phases of the treatment mixture.

For this reason, it is preferred that the concentration of sulfuric acid does not exceed 25 wt.-% based on the total weight of the cellulose-containing biomass present in the treatment mixture and is preferably kept as low as possible. This becomes even more important at higher processing temperatures, because higher processing temperatures also promote the formation of undesired by-products. Thus, the higher the processing temperature, the lower the concentration of sulfuric acid should be selected. A low concentration of sulfuric acid is also preferable with respect to subsequent enzymatic saccharification, because the enzyme activity decreases if the pH is too low. Accordingly, a low concentration of sulfuric acid in the treatment mixture allows direct subjection of the treatment mixture containing the treated cellulose-containing biomass to enzymatic saccharification without removal of the aqueous acid-containing liquid phase (see also below).

In this regard, it should be considered that other acids, if present in the treatment mixture, contribute to the decrease of the pH and may further promote the formation of undesired by-products. Accordingly, the total concentration of acids is preferably kept low. In this regard it is especially preferred that in said treatment mixture the amount of methanesulfonic acid is less than 100 wt.-%, preferably 90 wt.-% or less, preferably 50 wt.-% or less and more preferably 10 wt.-% or less, based on the weight of the sulfuric acid present in the treatment mixture, and preferably the treatment mixture does not contain more than 1 wt.-% of methanesulfonic acid based on the weight of the sulfuric acid present in the treatment mixture.

The pH value of the treatment mixture is preferably in a range of from 0 to 2.5, more preferably from 0.5 to 2.0.

The treatment mixture according to the invention comprises one or more compounds of formula (I)

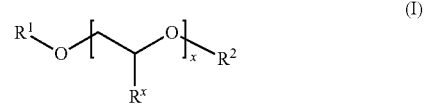

wherein in formula (I)
$R^1$ and $R^2$ are independently selected from the group consisting of hydrogen, methyl, ethyl, propyl and butyl
each $R^x$ in any of said x groups (II)

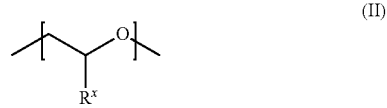

is independently of the meaning of $R^x$ in the other groups (II) selected from the group consisting of hydrogen, methyl, ethyl and propyl x is an integer from 50 to 250.

Within the compounds of formula (I) the groups (II)

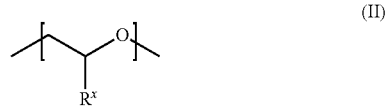
(II)

(wherein Rx is as defined above) are distributed either in a random manner, gradient manner or block-like.

Compounds of formula (I) with block-like distribution of the groups (II)

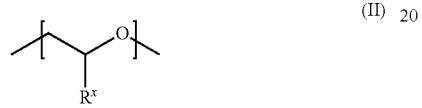
(II)

are obtainable by blockwise polyaddition of the corresponding alkylene oxide monomers.

Compounds of formula (I) with random distribution of the groups (II)

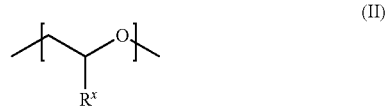
(II)

are obtainable by supplying the corresponding alkylene oxide monomers simultaneously to the reactor.

The group of compounds of formula (I) consists of compounds which are Surfactants and compounds which are not surfactants. Those compounds of formula (I) wherein the molecules each contain a hydrophilic region and a hydrophobic region are surfactants.

Preferred are compounds of formula (I) wherein $R^1$ is hydrogen or methyl and/or $R^2$ is selected from the group consisting of hydrogen, methyl, propy and butyl and/or each $R^x$ in any of said x groups (II) is independently of the meaning of $R^x$ in the other groups (II) selected from the group consisting of hydrogen, methyl, ethyl and propyl and/or x is an integer in the range from 50 to 210.

Further preferred are compounds of formula (I) wherein $R^1$ is hydrogen or methyl and $R^2$ is selected from the group consisting of hydrogen, methyl, propyl and butyl and each $R^x$ in any of said x groups (II) is independently of the meaning of $R^x$ in the other groups (II) selected from the group consisting of hydrogen, methyl, ethyl and propyl and x is an integer in the range from 50 to 210.

Further preferably (a) in one or more of said compounds of formula (I) $R^1$ and $R^2$ are selected from the group consisting of hydrogen and methyl, each $R^x$ is hydrogen and x is an integer in the range of from 70 to 210 or (b) in one or more of said compound of formula (I) $R^1$ is hydrogen or methyl, $R^2$ is selected from the group consisting of methyl, ethyl, propyl and butyl and each $R^x$ is either hydrogen or methyl wherein $R^x$=hydrogen and $R^x$=methyl are randomly distributed, wherein in each molecule of said compound of formula (I) the fraction of groups (II) wherein $R^x$ is methyl relative to the total amount of groups (II) is in the range of from 40 to 60% and x is an integer in the range of from 70 to 210 or (c) one or more of said compounds of formula (I) are selected from the group consisting of compounds of formula (I')

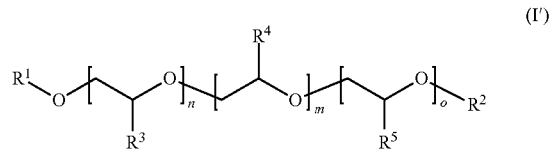
(I')

wherein $R^1$ and $R^2$ are hydrogen or methyl $R^3$, $R^4$ and $R^5$ are independently selected from the group consisting of hydrogen, methyl, ethyl and propyl with the proviso that all n $R^3$ are identical, all m $R^4$ are identical and all o $R^5$ are identical $R^4$ is not identical to $R^3$ and $R^4$ is not identical to $R^5$ n, m, o independently of each other are integers≥1 with the proviso that the sum of m, n and o is in the range of from 50 to 210.

In the above definitions of $R^1$, $R^2$ and $R^x$ propyl includes n-propyl and i-propyl, wherein n-propyl is preferred.

butyl includes n-butyl, i-butyl and t-butyl, wherein n-butyl is preferred.

With regard to the compounds of formula (I')

"all n $R^3$ are identical" means that in a molecule of a compound of formula (I') the number of groups $R^3$ is n and each of these $R^3$ is the same "all m $R^4$ are identical" means that in a molecule of a compound of formula (I') the number of groups $R^4$ is m and each of these $R^4$ is the same "and all o $R^5$ are identical" means that in a molecule of a compound of formula (I') the number of groups $R^5$ is o and each of these $R^5$ is the same More preferably, (a) in one or more of said compounds of formula (I) $R^1$ is hydrogen, $R^2$ is selected from the group consisting of hydrogen and methyl and each $R^x$ is hydrogen and x is an integer in the range of from 70 to 210 or (b) in one or more of said compounds of formula (I) $R^1$ is hydrogen, $R^2$ is selected from the group consisting of methyl, ethyl, n-propyl and n-butyl and each $R^x$ is either hydrogen or methyl wherein $R^x$=hydrogen and $R^x$=methyl are randomly distributed, wherein in each molecule of said compound of formula (I) the fraction of groups (II) wherein $R^x$ is methyl relative to the total amount of groups (II) is in the range of from 40 to 60% and x is an integer in the range of from 70 to 210 or (c) one or more of said compounds of formula (I) are selected from the group consisting of compounds of formula (I')

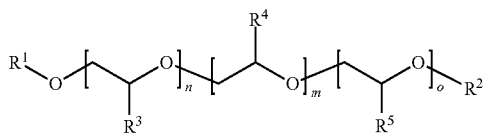

wherein $R^1$ and $R^2$ are hydrogen $R^3$, $R^4$ and $R^5$ are independently selected from the group consisting of hydrogen and methyl with the proviso that all n $R^3$ are identical, all m $R^4$ are identical and all o $R^5$ are identical $R^4$ is not identical to $R^3$ and $R^4$ is not identical to $R^5$ n, m, o independently of each other are integers≥1 with the proviso that the sum of m, n and o is in the range of from 50 to 210.

Particularly preferably, (a) in one or more of said compounds of formula (I) $R^1$, $R^2$ and each $R^x$ are hydrogen and x is an integer in the range of from 70 to 210 (Suitable Compounds of formula (I) of this preferred group are available under the trade name Pluriol® E from BASF SE)

or (b) in one or more of said compounds of formula (I) $R^1$ is hydrogen, $R^2$ is selected from the group consisting of n-propyl and n-butyl and each $R^x$ is either hydrogen or methyl wherein $R^x$=hydrogen and $R^x$=methyl are randomly distributed, wherein in each molecule of said compound of formula (I) the fraction of groups (II) wherein $R^x$ is methyl relative to the total amount of groups (II) is in the range of from 40 to 60% and x is an integer in the range of from 100 to 150 (Suitable Compounds of formula (I) of this preferred group are available under the trade name Pluriol® A from BASF SE).

or (c) one or more of said compounds of formula (I) are selected from the group consisting of compounds of formula (I')

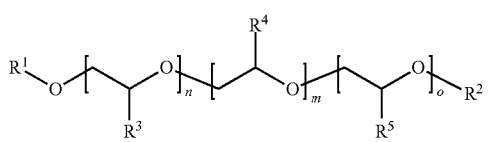

wherein $R^1$ and $R^2$ are hydrogen all $R^3$ and $R^5$ are hydrogen all $R^4$ are methyl n, m, o independently of each other are integers≥1 with the proviso that the sum of m, n and o is in the range of from 50 to 200 and preferably n=o (Suitable compounds of formula (I') of this preferred group are available under the trade name Pluronic® from BASF).

Especially preferred compounds of formula (I') are those wherein $R^1$, $R^2$, all $R^3$ and all $R^5$ are hydrogen and $R_4$ is methyl, m is an integer in the range of from 25 to 35 and n and o are integers in the range of from 65 to 85, wherein preferably n+o (sum of n and o) is 140 to 160, m is an integer in the range of from 25 to 35, and n and o are integers in the range of from 12 to 15, wherein preferably n+o (sum of n and o) is 25 to 30 wherein in each case preferably n and o are identical.

Preferably the one or more compounds of formula (I) as defined above are water-soluble.

Preferably the total concentration of compounds of formula (I) in said treatment mixture is in the range of from 0.05 wt.-% to 25 wt.-%, more preferably 0.1 wt.-% to 12 wt.-%, most preferably 0.5 wt.-% to 8 wt.-% in each case based on the total weight of the cellulose-containing biomass present in the treatment mixture.

At a concentration below 0.05 wt.-% based on the total weight of the cellulose-containing biomass present in the treatment mixture, the amount of compounds selected from the group consisting of compounds of formula (I) in the treatment mixture is too low so that said compounds have no significant effect on the yield of glucose in subsequent saccharification, compared to treated cellulose-containing biomass obtained by processing under identical conditions with the sole exception that the treatment mixture does not comprise any compound of formula (I). For economical reasons, the concentration of compounds of formula (I) is preferably not more than 25 wt.-% based on the total weight of the cellulose-containing biomass present in the treatment mixture. Furthermore, certain compounds of formula (I) behave as surfactants, and at a high concentration of surfactants foam may be formed in the treatment mixture, which is detrimental for processing the treatment mixture.

Preferably, in the treatment mixture the total amount of cellulose-containing biomass, water, sulfuric acid and compounds of formula (I) is at least 95 wt.-%, preferably at least 98 wt.-% more preferably at least 99 wt.-% based on the total weight of the treatment mixture.

Preferably the treatment mixture used in the method according to the invention is obtained by adding an aqueous treatment solution containing sulfuric acid and one or more compounds of formula (I) to said cellulose-containing biomass.

Preferably the above defined aqueous treatment solution is added to the cellulose-containing biomass in such amount that a treatment mixture is obtained comprising 3 wt.-% to 75 wt.-%, more preferably 8 wt.-% to 70 wt.-%, further preferably 15 wt.-% to 60 wt.-%, most preferably 25 wt.-% to 50 wt.-%, particularly preferably 30 wt.-% to 45 wt.-% of cellulose containing biomass, in each case based on the total weight of said treatment mixture.

Preferably, the concentration of sulfuric acid in said aqueous treatment solution is in the range of from 0.1 wt.-% to 5.5 wt.-%, preferably 0.2 wt.-% to 5.0 wt.-%, more preferably 0.3 wt.-% to 3.0 wt.-%, most preferably 0.4 wt.-% to 1.5 wt.-% in each case based on the total weight of said aqueous treatment solution.

Preferably the total concentration of compounds of formula (I) in said aqueous treatment solution is in the range of from 0.01 wt.-% to 5 wt.-%, preferably 0.05 wt.-% to 3.0 wt.-%, more preferably 0.1 wt.-% to 2.0 wt.-%, most preferably 0.1 wt.-% to 1.0 wt.-% in each case based on the total weight of said aqueous treatment solution.

Further preferably, in said aqueous treatment solution
the concentration of sulfuric acid is in the range of from 0.1 wt.-% to 5.5 wt.-%, preferably 0.2 wt.-% to 5.0 wt.-%, more preferably 0.3 wt.-% to 3.0 wt.-%, most preferably 0.4 wt.-% to 1.5 wt.-% and the total concentration of compounds of formula (I) in said aqueous treatment solution is in the range of from 0.01 wt.-% to 5 wt.-%, preferably 0.05 wt.-% to 3.0 wt.-%, more preferably 0.1 wt.-% to 2.0 wt.-%, most preferably 0.1 wt.-% to 1.0 wt.-% in each case based on the total weight of said aqueous treatment solution.

Processing Conditions

In the method of the present invention said treatment mixture is subjected to a temperature in the range of from 100° C. to 220° C., wherein the pressure is selected so that at least a part of the water is in the liquid state.

When the temperature is below 100° C., the yield of glucose obtainable by saccharification of said treated cellulose-containing biomass is significantly reduced. When the temperature is above 220° C., the amount of undesirable by-products resulting from decomposition of cellulose and/or hemicellulose, like furanes, furfural and hydroxymethyl furfural, is too high. Formation of these by-products reduces the amount of cellulose available for saccharification and/or inhibits the activity of the enzymes needed for the enzymatic saccharification.

Regarding the selection of the pressure, it is important that the pressure is sufficiently high to avoid complete vaporization of the water, so as to allow interaction between the cellulose-containing biomass and the sulfuric acid dissolved in water. On the other hand, for economical and technical reasons the pressure is preferably as low as possible.

Preferably, in the method according to the present invention a temperature in the range of from 100° C. to 220° C. at a pressure in the range of from 100 kPa to 4000 kPa (wherein the pressure is selected so that at least a part of the water is in the liquid state) is maintained for a duration of not more than 120 minutes, preferably of not more than 60 minutes, further preferably of not more than 30 minutes, particularly preferably of not more than 20 minutes and most preferably of not more than 10 minutes. Thereafter the treatment mixture is allowed to cool and/or the pressure is lowered.

Preferably the temperature is in a range of 110° C. to 180° C., preferably of 120° C. to 175° C. Preferably, the pressure is in a range of 100 kPa to 1600 kPa, further preferably of 100 kPa to 1300 kPa, more preferably of 100 kPa to 1000 kPa. Further preferably, the temperature is in a range of 110° C. to 180° C., preferably 120° C. to 175° C., and the pressure is in a range of from 100 kPa to 1600 kPa, preferably 100 kPa to 1300 kPa, more preferably 100 kPa to 1000 kPa.

The skilled person is aware of the interdependence between the parameters concentration of sulfuric acid, temperature and duration of treatment. Thus, the lower the concentration of sulfuric acid the higher the temperature and/or the duration of the treatment have to be selected and vice versa (see also above). Based on his knowledge, the skilled person will select the parameters accordingly, or determine the suitable combination of said parameters by simple routine experimentation.

Especially preferred is a method of the invention wherein two or more, preferably all of the above-described preferred features regarding the processing conditions are combined.

Further preferred is a method of the invention wherein two or more, preferably all of the above-described preferred features regarding the processing conditions and the composition of the treatment mixture are combined.

In this regard especially preferred is a method according to the present invention comprising the steps of preparing an aqueous treatment solution containing 0.4 wt.-% to 1.5 wt.-% of sulfuric acid and 0.1 wt.-% to 1 wt.-% of one or more compounds of formula (I)

adding said aqueous treatment solution to said cellulose-containing biomass so that a treatment mixture comprising said cellulose-containing biomass, water and sulfuric acid and one or more compounds of formula (I) is obtained, said treatment mixture comprising 30 wt.-% to 45 wt.-% of cellulose containing biomass, based on the total weight of said treatment mixture subjecting said treatment mixture to a temperature in the range of from 120° C. to 175° C., wherein said temperature is maintained for a duration of not more than 40 minutes to generate a treated cellulose-containing biomass.

In the above-defined method, the one or more compounds of formula (I) are preferably selected among the above-defined preferred compounds of formula (I).

Processing Equipment

In order to allow for an efficient processing of cellulose-containing biomass according to the present invention, it is important that the solid constituents of the reaction mixture are in intimate contact with the liquid phase of the reaction mixture and—if present—steam formed by partial vaporization of the water of the mixture. This intimate contact preferably exists all the time the reaction mixture is subjected to a temperature in the range of from 100° C. to 220° C. at a pressure in the range of from 100 kPa to 4000 kPa (wherein the pressure is selected so that at least a part of the water is in the liquid state). Accordingly, for the method of the present invention, any type of reactor may be used which allows meeting this condition.

More specifically a rotating reactor, e.g. in the form of a rotating drum may be used. Alternatively, a reactor having means for mixing the reactants may be used, e.g. a stirred tank reactor. Different mixing means are applicable e.g. pug mixer, paddle mixer, ribbon mixer.

Another suitable type of reactor is a percolation reactor wherein the cellulose-containing biomass is maintained in a fixed bed, e.g. a column, a tube, a drum or a vessel, and the aqueous treatment solution comprising sulfuric acid and one or more compounds of formula (I) is flowed through the bed, e.g. a trickle-bed reactor type which allows for liquid flow involving relatively small volume of liquid. Preferably, the reactor is designed so as to allow for recirculation of the aqueous treatment solution comprising sulfuric acid and one or more compounds of formula (I).

A further suitable type of reactor is a screw-type reactor. In such type of reactor, radial mixing of solids (i.e. the cellulose-containing biomass) is provided along the length of the reactor shaft, and the aqueous treatment solution comprising sulfuric acid and one or more compounds of formula (I) is either in co-current or in counter-current flow to the solids. If present, steam formed by partial vaporization of the water of the aqueous treatment solution is a further constituent of said co-current or counter-current flow to the solids.

Combinations of above mentioned reactor types are possible, too.

The method may be operated in a discontinuous, semi-continuous or continuous operation mode.

Heating of the treatment mixture to the desired processing temperature is achieved by means of electric heating, steam or other suitable means known to those skilled in the art.

The reactor may be designed as a single step reactor so that for further processing steps like saccharification the treated cellulose-containing biomass is removed from the reactor and transferred to one or more further reactors wherein such further processing steps are carried out. Alternatively, the reactor may be designed as a multi-step reactor allowing for subsequent saccharification of the treated cellulose-containing biomass without taking the treated cellulose-containing biomass out of the reactor.

Further Processing Steps

Preferably, the method according to the present invention further comprises a step selected from the group consisting of saccharification of the treated cellulose-containing biomass so that glucose and/or other sugars are formed and optionally fermentation and/or chemical processing of the formed glucose and/or other sugars, and further processing of the treated cellulose-containing biomass to obtain dissolving pulp.

In a first preferred alternative, saccharification of the treated cellulose-containing biomass is effected by means of enzymes (enzymatic saccharification, sometimes also referred to as enzymatic hydrolysis step). In the step of enzymatic saccharification suitable enzymes are added to the treated cellulose-containing biomass to convert the contained cellulose to glucose and/or other sugars, e.g. xylose. Suitable reactors, processing conditions and enzymes for the enzymatic saccharification are known to those skilled in the art. The enzymatic saccharification step is generally performed in stirred-tank reactors or fermentors under controlled pH, temperature, and mixing conditions. The enzymatic saccharification step may last up to 200 hours. Enzymatic saccharification is usually carried out at temperatures from about 30° C. to about 65° C., in particular around 50° C., and at a pH in the range of from about 4 and about 6, especially around pH 5.5. To produce glucose that can be metabolized by yeast, the enzymatic saccharification is typically performed in the presence of a beta-glucosidase enzyme. Preferably an enzyme formulation comprising one or more enzymes selected from the group consisting of beta-glucosidases, exo-cellobiohydrolases, endo- and exo-glucanases, glucoside hydrolases and xylanases is used. In some cases it is preferable to use enzymes which are thermally stable and allow to the enzymatic saccharification to be carried out at temperatures from about 60° C. to about 80° C.

In a second preferred alternative, saccharification is achieved by chemical, especially thermochemical, processing of the treated cellulose-containing biomass, said chemical processing not involving enzymes. More specifically, fermentable sugars and lignin are producible from the treated cellulose-containing biomass (obtainable by the method of the present invention) by treatment with a supercritical or near-supercritical fluid or by hydrothermal treatment.

The sugars obtained by saccharification of the treated cellulose-containing biomass may serve as feedstock for obtaining a plurality of further products, either by fermentation or by chemical processing of the sugars obtained by saccharification of the treated cellulose-containing biomass.

In the fermentation step, glucose obtained by saccharification of the treated cellulose-containing biomass is fermented to ethanol by a fermenting organism, such as yeast. Suitable reactors, processing conditions and fermenting organisms for the fermentation are known to those skilled in the art. The steps of enzymatic saccharification and of fermentation are performed simultaneously in one vessel or in separate vessels. In the first alternative, the fermentation is carried out simultaneously with the enzymatic saccharification in the same vessel under controlled pH, temperature, and mixing conditions. Typical products of the fermentation of glucose include ethanol, butanol, butanediol, lactic acid, amino acids and succinic acid.

Chemical processing of sugars obtained by saccharification of the treated cellulose-containing biomass refers to processes wherein said sugars are subjected to a chemical reaction not involving fermentation to obtain other chemical products. Preferably, said chemical reaction is carried out in the presence of one or more catalysts which are not enzymes. Typical products obtainable by chemical processing of glucose include sugar alcohols, sugar acids, hydroxymethylfurfural and derivatives thereof.

In a preferred method of the present invention, the liquid phase of the treatment mixture is at least partially separated from the treated cellulose-containing biomass prior to saccharification of the treated cellulose-containing biomass, e.g. by filtration and subsequent washing of the treated cellulose-containing biomass. The liquid phase of the treatment mixture consists of an aqueous solution, which contains hemicellulosic sugars (e.g. xylose) and further water-soluble decomposition products formed in the step of subjecting the treatment mixture to a temperature in the range of from 100° C. to 220° C. at a pressure in the range of from 100 kPa to 4000 kPa. This aqueous solution may be used as a feedstock for further processes. Typical products obtainable by chemical processing of xylose include sugar alcohols, sugar acids, furfural and derivatives thereof.

Separating the liquid constituents of the treatment mixture from the treated cellulose-containing biomass prior to enzymatic saccharification has the advantage that water-soluble by-products like furanes, furfural and hydroxymethylfurfural which may act as enzyme inhibitors are removed from the treated cellulose-containing biomass which is subjected to enzymatic separation. A disadvantage of this specific method is that the compounds of formula (I) may be removed from the treated cellulose-containing biomass so that any possible positive effect (as described above) of the presence of compounds of formula (I) during enzymatic saccharification may be reduced.

In an alternative preferred method according to the present invention the enzymes for the saccharification are added to the treatment mixture comprising the treated cellulose-containing biomass without prior removal of the liquid phase from the treated cellulose-containing biomass, thus reducing complexity of the overall processing method. Furthermore, in this method the compounds of formula (I) remain in the treated cellulose-containing biomass so that the above-described positive effects may be obtained as much as possible. For this specific method of the present invention, it is especially important that the acid concentration in the treatment mixture is low and that the step of subjecting the treatment mixture to a temperature in the range of from 100° C. to 220° C. at a pressure in the range of from 100 kPa to 4000 kPa is carried out in such manner that the amount of by-products like furanes, furfural and hydroxymethylfurfural which may act as enzyme inhibitors is as small as possible. If necessary the acid in the treatment mixture is neutralized to adjust the pH to a value suitable for enzymatic saccharification.

Another field of application of the present invention is related to the production of dissolving pulp. Dissolving pulp (also called dissolving cellulose) is a bleached wood pulp or cotton linters having a high content of cellulose (>90%). It has a high level of brightness and uniform molecular-weight distribution. This pulp is manufactured for uses that require a high chemical purity, and particularly low hemicellulose content, since the hemicellulose can interfere with subsequent processes. Dissolving pulp is so named because it is not made into paper, but dissolved either in a solvent or by derivatization into a homogeneous solution, which makes it completely chemically accessible and removes any remaining fibrous structure. Once dissolved, it can be spun into textile fibers, or chemically reacted to produce derivatized celluloses, such as cellulose triacetate, a plastic-like material formed into fibers or films, or cellulose ethers such as methyl cellulose, used as a thickener. Dissolving pulp is mainly produced chemically from the pulpwood by the sulfite process or the kraft process with an acid prehydrolysis step to at remove hemicelluloses. As noted above, in the treated cellulose-containing biomass obtainable by the method of the present invention the content of hemicellulose and/or lignin is typically decreased due to decomposition to xylose. Therefore, the treated cellulose-containing biomass obtainable by the method of the present invention is suitable for further processing to obtain dissolving pulp.

Hereinbelow the invention is described further by means of examples.

EXAMPLES

1. Pretreatment of Cellulose-containing Biomass:

An autoclave with an anchor stirrer is filled with a treatment mixture consisting of
  an amount of chopped straw as specified in table 1 below, and an aqueous treatment solution comprising sulfuric acid in the concentration specified in tables 1-4 (examples 6-9, 12-14, 16-18, 20) and optionally either a compound of formula (I) or a comparison additive which is not a compound of formula (I) (examples 2-5 and 11) as specified in type and concentration in table 1-4.

In the above-defined treatment mixture, the weight fraction of chopped straw corresponds to 5% of the total weight of the treatment mixture, and the weight fraction of the aqueous treatment solution corresponds to 95% of the total weight of the treatment mixture.

Hereinbelow, the compounds of formula (I) and the comparison additives which are not compounds of formula (I) are commonly referred to as additives. For the chemical structure of said additives, see table 5 hereinbelow. All additives are commonly used surfactants which are commercially available. For comparison, examples 1, 10, 15, 19, 21 and 22 are carried out using an aqueous treatment solution comprising sulfuric acid in the concentration specified in tables 1-4 and no additive.

For preparing the above-defined aqueous treatment solutions, an aqueous solution comprising 96 wt.-% sulfuric acid is diluted with deionized water.

The autoclave is purged three times with nitrogen gas and the treatment mixture is heated to the target temperature specified in tables 1-4 under stirring (50 rpm). The resulting pressure is in the range of 280 kPa to 340 kPa. After reaching the target temperature, the temperature is maintained for the time interval according to tables 1-4. Thereafter heating is turned off, the mixture is allowed to cool to ambient temperature, and then the autoclave is relaxed and is emptied.

The obtained mixture comprising treated cellulose-containing biomass is filtered through a frit (pore size 2), and the weight of the liquid phase obtained as filtrate is determined, see tables 1-4. The weight of the treated cellulose-containing biomass (solid phase) obtained as filtration residue is determined, see tables 1-4, and then a sample of the obtained treated cellulose-containing biomass is subjected to enzymatic saccharification as described herein below.

2. Enzymatic Saccharification of Cellulose-containing Biomass:

4.50 g of the treated cellulose-containing biomass obtained as described above are weighed into a 50 mL tube and filled up with deionized water containing 0.1 wt.-% sodium azide to a volume of 30 mL. A pH-value of 5.5 is adjusted by adding 100 mM phosphate buffer and an enzyme formulation comprising one or more enzymes selected from the group consisting of beta-glucosidases, exo-cellobiohydrolases, endo- and exo-glucanases, glucoside hydrolases and xylanases is added in the concentration as specified in tables 1-4. Optionally a compound of formula (I), as specified in type and concentration in table 4 is added to the saccharification solution (examples 21 and 22). The mixture is incubated in an Eppendorf-Thermomixer at 350 rpm and 53° C. (50° C. internal). At certain intervals specified in tables 1-4, 1 mL samples were withdrawn and diluted 1:1 with water. After centrifugation of the sample the clear supernatant is analyzed by HPLC for the concentrations of glucose and xylose.

The "yields" as indicated in tables 1-4 are either absolute yields stated in arbitrary units or normalized absolute yields. Thus, the yields in tables 1-4 are not based on a theoretical yield. The yields of glucose obtained after 24 hours and 48 hours of enzymatic saccharification are extrapolated to the quantity of treated cellulose-containing biomass and normalized with respect to the yield after 24 hours of enzymatic saccharification according to the corresponding comparison example (pretreatment using an aqueous treatment solution comprising sulfuric acid and no additive).

Table 1 shows a series of experiments (examples 1-9) wherein pretreatment and enzymatic saccharification is carried out under the same conditions with the exception of the additive in the treatment mixture. For comparison example 1 is provided wherein the aqueous treatment solution does not contain any additive. Surprisingly it has been found that the presence of a compound of formula (I) in the treatment mixture results in a higher yield of glucose after 24 and 48 hours of enzymatic saccharification (examples 6-9), compared to example 1 where no additive is present in the treatment mixture. On the other hand, the presence of a comparison additive in the treatment mixture (examples 2-5) instead of a compound of formula (I) results in a significantly lower increase of the yield of glucose after 24 hours and 48 hours of enzymatic saccharification.

Table 2 shows another series of experiments (examples 101-14) wherein pretreatment and enzymatic saccharification is carried out under the same conditions with the exception of the additive in the treatment mixture. Again, it has been found that the presence of a compound of formula (I) in the treatment mixture results in a higher yield of glucose after 24 and 48 hours of enzymatic saccharification (examples 12-14), compared to example 10 where no additive is present in the treatment mixture, and to example 11, where a comparison additive is present in the treatment mixture. Indeed the presence of the comparison additive of example 11 results in a slight decrease of the yield of glucoses after 24 hours of saccharification.

The results of tables 1 and 2 indicate a strong influence of the chemical structure of such additives in the treatment mixture. Furthermore, the table 1 shows the effect of the molecule size. Although the additives of examples 4 to 8 are have a similar chemical structure, the additives of examples 4 and 5, which have a lower amount of ethylene oxide units than the additives of examples 6 to 8, have an inferior effect. Due to their low number of ethylene oxide units, the additives of examples 4 and 5 are not compounds of formula (I) as defined above.

Table 3 shows a series of experiments (examples 16-18) wherein the influence of the enzyme dosage on the yield of glucose is demonstrated. From example 16 to 18 the enzyme dosage is reduced successively. For comparison example 15 is provided wherein the aqueous treatment solution does not contain any additive and the enzyme dosage is identical to example 16. In examples 15-18, all other parameters of pretreatment and enzymatic saccharification are identical (the different starting mass of chopped straw is compensated for by a larger amount of aqueous treating solution so as to adjust the above-defined weight fractions of chopped straw and aqueous treatment solution in the treatment mixture). The results show that even in example 18 with an enzyme dosage of only 25% of that of examples 15 and 16 the yield of glucose is significantly higher than in example 15. This indicates that the pretreatment according to the method of the present invention allows for a reduction of the enzyme dosage in enzymatic saccharification of the treated cellulose containing biomass without compromising the yield of glucoses. This is a significant advantage because the costs of the enzyme formulation needed for the enzymatic saccharification are quite high and form a serious obstacle against the broad application of enzymatic processes.

Table 4 shows a series of experiments (examples 20-22) wherein the influence of the point in time when the compound of formula (I) is added is demonstrated. In example 20, a compound of formula (I) is present in the treatment mixture. In comparison examples 21 and 22 no compound of formula (I) is present in the treatment mixture, but a compound of formula (I) is added to the saccharification solution in the concentration specified in table 4. This approach is described in the publication Bioresource Technology 169 (2014) 713-722. For further comparison example 19 is provided wherein neither the treatment mixture nor the saccharification solution contains any additive. In examples 19-22, all other parameters of pretreatment and enzymatic saccharification are identical (the different starting mass of chopped straw is compensated for by a larger amount of aqueous treating solution so as to adjust the above-defined weight fractions of chopped straw and aqueous treatment solution in the treatment mixture). The results show that the presence of a compound of formula (I) in the saccharification solution has only a very low effect on the yield of glucose, even if the concentration of said compound of formula (I) in the saccharification solution is significantly higher (example 22) than the concentration of said compound of formula (I) in the treatment mixture used in parallel example 20. This finding shows that the method according to the present invention provides a more efficient approach for increasing the yield of glucose, compared to the approach described in Bioresource Technology 169 (2014) 713-722.

It is noted that in the above-described examples the concentration of cellulose-containing biomass based on the total weight of the treatment mixture is rather close to the lower limit of the above-defined preferred range of 3 wt.-% to 75 wt.-%. However it is common practice in the technical field of the present invention that the effect of an additive with respect to biomass is initially studied in the presence of a low concentration of biomass. Based on the results gained from the examples described herein, the skilled person based on his knowledge is capable of routinely scaling up the method of the present invention to higher concentrations of cellulose-containing biomass.

TABLE 1

| | Example No. | | | | | | | | |
|---|---|---|---|---|---|---|---|---|---|
| | 1 | 2 | 3 | 4 | 5 | 6 | 7 | 8 | 9 |
| Pretreatment of chopped straw to give treated cellulose-containing biomass | | | | | | | | | |
| Mass of chopped straw/g | 7.5 | 7.5 | 7.5 | 7.5 | 7.5 | 7.5 | 7.5 | 7.5 | 7.5 |
| Sulfuric acid conc./wt.-% of aqueous treatment solution | 0.35 | 0.35 | 0.35 | 0.35 | 0.35 | 0.35 | 0.35 | 0.35 | 0.35 |
| Additive type and conc./wt.-% of aqueous treatment solution | / | 0.25% Additive 1 | 0.25% Additive 3 | 0.25% Additive 4 | 0.25% Additive 5 | 0.25% Additive 6 | 0.25% Additive 7 | 0.25% Additive 8 | 0.25% Additive 9 |
| Temperature/° C. | 155 | 155 | 155 | 155 | 155 | 155 | 155 | 155 | 155 |
| Hold time at target temperature/min | 0 | 0 | 0 | 0 | 0 | 0 | 0 | 0 | 0 |
| Liquid phase (filtrate)/g | 112.8 | 121.2 | 106.2 | 118.8 | 114.6 | 114.2 | 111.5 | 113.7 | 123.9 |
| solid phase (filtration residue)/g | 27.3 | 22.9 | 37.4 | 21.8 | 24.1 | 25.6 | 27.1 | 25.8 | 20.9 |
| Enzymatic saccharification | | | | | | | | | |
| Used treated cellulose-containing biomass/g | 4.50 | 4.50 | 4.50 | 4.50 | 4.50 | 4.50 | 4.50 | 4.50 | 4.50 |
| Enzyme dosage/ mg Protein per g dry treated cellulose-containing biomass | 5 | 5 | 5 | 5 | 5 | 5 | 5 | 5 | 5 |
| Glucose concentration after 24 h/mg/mL | 9.63 | 12.23 | 8.21 | 12.52 | 11.86 | 13.03 | 12.24 | 12.51 | 15.84 |
| Glucose concentration after 48 h/mg/mL | 10.76 | 13.23 | 8.51 | 14.00 | 13.21 | 14.11 | 13.22 | 13.98 | 17.54 |
| Calculations | | | | | | | | | |
| factor cellulose-containing biomass 'treated/used in saccharification' | 6.07 | 5.09 | 8.31 | 4.84 | 5.36 | 5.69 | 6.02 | 5.73 | 4.64 |
| Extrapolated yield of glucose from treated cellulose-containing biomass/absolute | | | | | | | | | |
| Glucose after 24 h enzymatic saccharification/mg/mL | 58.40 | 62.25 | 68.20 | 60.65 | 63.49 | 74.14 | 73.70 | 71.70 | 73.59 |
| Glucose after 48 h enzymatic saccharification/mg/mL | 65.29 | 67.31 | 70.71 | 67.80 | 70.74 | 80.30 | 79.64 | 80.14 | 81.45 |

TABLE 1-continued

|  | Example No. | | | | | | | | |
|---|---|---|---|---|---|---|---|---|---|
|  | 1 | 2 | 3 | 4 | 5 | 6 | 7 | 8 | 9 |
| Norm: Glucose after 24 h enzymatic saccharification/ (pretreatment without additive) | 58.40 | 58.40 | 58.40 | 58.40 | 58.40 | 58.40 | 58.40 | 58.40 | 58.40 |
| Yield of glucose from treated cellulose-containing biomass/normalized | | | | | | | | | |
| Glucose after 24 h enzymatic saccharification | 1.00 | 1.07 | 1.17 | 1.04 | 1.09 | 1.27 | 1.26 | 1.23 | 1.26 |
| Glucose after 48 h enzymatic saccharification | 1.12 | 1.15 | 1.21 | 1.16 | 1.21 | 1.37 | 1.36 | 1.37 | 1.39 |

TABLE 2

| Example No. | 10 | 11 | 12 | 13 | 14 |
|---|---|---|---|---|---|
| Pretreatment of chopped straw to give treated cellulose-containing biomass | | | | | |
| Mass of chopped straw/g | 7.5 | 7.5 | 7.5 | 7.5 | 7.5 |
| Sulfuric acid conc./wt.-% of aqueous treatment solution | 0.35 | 0.35 | 0.35 | 0.35 | 0.35 |
| Additive type and conc./wt.-% of aqueous treatment solution | / | 0.25% Additive 2 | 0.25% Additive 10 | 0.25% Additive 11 | 0.25% Additive 6 |
| Temperature/° C. | 155 | 155 | 155 | 155 | 155 |
| Hold time at target temperature/min | 0 | 0 | 0 | 0 | 0 |
| Liquid phase (filtrate)/g | 115.9 | 118.4 | 112.2 | 119.6 | 115.8 |
| solid phase (filtration residue)/g | 25.3 | 24.1 | 30.0 | 25.1 | 26.5 |
| Enzymatic saccharification | | | | | |
| Used treated cellulose-containing biomass/g | 4.50 | 4.50 | 4.50 | 4.50 | 4.50 |
| Enzyme dosage/mg Protein per g dry treated cellulose-containing biomass | 5 | 5 | 5 | 5 | 5 |
| Glucose concentration after 24 h/mg/mL | 7.70 | 7.82 | 8.80 | 10.81 | 12.67 |
| Glucose concentration after 48 h/mg/mL | 8.48 | 9.18 | 11.18 | 12.59 | 14.12 |
| Calculations | | | | | |
| factor cellulose-containing biomass 'treated/used in saccharification' | 5.62 | 5.36 | 6.67 | 5.58 | 5.89 |
| Extrapolated yield of glucose from treated cellulose-containing biomass/absolute | | | | | |
| Glucose after 24 h enzymatic saccharification/mg/mL | 43.27 | 41.89 | 58.69 | 60.31 | 74.61 |
| Glucose after 48 h enzymatic saccharification/mg/mL | 47.70 | 49.17 | 74.53 | 70.22 | 83.14 |
| Norm: Glucose after 24 h enzymatic saccharification/pretreatment without additive | 43.27 | 43.27 | 43.27 | 43.27 | 43.27 |
| Yield of glucose from treated cellulose-containing biomass/normalized | | | | | |
| Glucose after 24 h enzymatic saccharification | 1.00 | 0.97 | 1.36 | 1.39 | 1.72 |
| Glucose after 48 h enzymatic saccharification | 1.10 | 1.14 | 1.72 | 1.62 | 1.92 |

TABLE 3

| Example No. | 15 | 16 | 17 | 18 |
|---|---|---|---|---|
| Pretreatment of chopped straw to give treated cellulose-containing biomass | | | | |
| Mass of chopped straw/g | 15 | 22.5 | 22.5 | 22.5 |
| Sulfuric acid conc./wt.-% of aqueous treatment solution | 0.35 | 0.35 | 0.35 | 0.35 |
| Additive type and conc./wt.-% of aqueous treatment solution | / | 0.25% Additive 6 | 0.25% Additive 6 | 0.25% Additive 6 |
| Temperature/° C. | 155 | 155 | 155 | 155 |
| Hold time at target temperature/min | 0 | 0 | 0 | 0 |
| Liquid phase(filtrate)/g | 242.7 | 364.5 | 364.5 | 364.5 |
| solid phase (filtration residue)/g | 38.7 | 66.4 | 66.4 | 66.4 |
| Enzymatic saccharification | | | | |
| Used treated cellulose-containing biomass/g | 4.50 | 4.50 | 4.50 | 4.50 |
| Enzyme dosage/mg Protein per g dry treated cellulose-containing biomass | 5 | 5 | 2.5 | 1.25 |
| Glucose concentration after 24 h/mg/mL | 13.11 | 15.25 | 13.50 | 9.71 |
| Glucose concentration after 48 h/mg/mL | 14.09 | 15.50 | 14.65 | 12.44 |
| Calculations | | | | |
| factor cellulose-containing biomass 'treated/used in saccharification' | 8.60 | 14.76 | 14.76 | 14.76 |

TABLE 3-continued

| Example No. | 15 | 16 | 17 | 18 |
|---|---|---|---|---|
| Extrapolated yield of glucose from treated cellulose-containing biomass/absolute | | | | |
| Glucose after 24 h enzymatic saccharification/mg/mL | 112.75 | 224.95 | 199.19 | 143.34 |
| Glucose after 48 h enzymatic saccharification/mg/mL | 121.21 | 228.65 | 216.17 | 183.54 |
| Norm: Glucose after 24 h enzymatic saccharification/pretreatment without additive | 112.75 | 112.75 | 112.75 | 112.75 |
| Yield of glucose from treated cellulose-containing biomass/normalized | | | | |
| Glucose after 24 h enzymatic saccharification | 1.00 | 2.00 | 1.77 | 1.27 |
| Glucose after 48 h enzymatic saccharification | 1.08 | 2.03 | 1.92 | 1.63 |

TABLE 4

| Example No. | 19 | 20 | 21 | 22 |
|---|---|---|---|---|
| Pretreatment of chopped straw to give treated cellulose-containing biomass | | | | |
| Mass of chopped straw/g | 15 | 22.5 | 15 | 15 |
| Sulfuric acid conc./wt.-% of aqueous treatment solution | 0.35 | 0.35 | 0.35 | 0.35 |
| Additive type and conc./wt.-% of aqueous treatment solution | / | 0.25% Additive 6 | / | / |
| Temperature/° C. | 155 | 155 | 155 | 155 |
| Hold time at target temperature/min | 0 | 0 | 0 | 0 |
| Liquid phase (filtrate)/g | 242.7 | 364.5 | 242.7 | 242.7 |
| solid phase (filtration residue)/g | 38.7 | 66.4 | 38.7 | 38.7 |
| Enzymatic saccharification | | | | |
| Used treated cellulose-containing biomass/g | 4.50 | 4.50 | 4.50 | 4.50 |
| Enzyme dosage/mg Protein per g dry treated cellulose-containing biomass | 5 | 5 | 5 | 5 |
| Additive type and conc./wt.-% of saccharification solution | / | / | 0.25% Additive 6 | 5.00% Additive 6 |
| Glucose concentration after 24 h/mg/mL | 13.11 | 15.25 | 13.29 | 14.09 |
| Glucose concentration after 48 h/mg/mL | 14.09 | 15.50 | 14.08 | 14.68 |
| Calculations | | | | |
| factor cellulose-containing biomass 'treated/used in saccharification' | 8.60 | 14.76 | 8.60 | 8.60 |
| Extrapolated yield of glucose from treated cellulose-containing biomass/absolute | | | | |
| Glucose after 24 h enzymatic saccharification/mg/mL | 112.75 | 224.95 | 114.29 | 121.17 |
| Glucose after 48 h enzymatic saccharification/mg/mL | 121.21 | 228.65 | 121.08 | 126.22 |
| Norm: Glucose after 24 h enzymatic saccharification/pretreatment without additive | 112.75 | 112.75 | 112.75 | 112.75 |
| Yield of glucose from treated cellulose-containing biomass/normalized | | | | |
| Glucose after 24 h enzymatic saccharification | 1.00 | 2.00 | 1.01 | 1.07 |
| Glucose after 48 h enzymatic saccharification | 1.08 | 2.03 | 1.07 | 1.12 |

TABLE 5

| Additive name | Compound of formula (I) | Chemical structure |
|---|---|---|
| Additive 1 | no | Alkyl polyglucoside based on natural plant origin $C_8$-$C_{10}$ fatty alcohols |
| Additive 2 | no | Alkyl polyglucoside based on natural plant origin $C_8$-$C_{14}$ fatty alcohols |
| Additive 3 | no | polyoxyethylene(20) sorbitan monolaurate |
| Additive 4 | no | polyethylene glycol having an average molecular weight of about 300 g/mol |
| Additive 5 | no | polyethylene glycol having an average molecular weight of 1000 g/mol |
| Additive 6 | yes | polyethylene glycol having an average molecular weight of 3400 g/mol |
| Additive 7 | yes | polyethylene glycol having an average molecular weight of 6000 g/mol |
| Additive 8 | yes | polyethylene glycol having an average molecular weight of 9000 g/mol |
| Additive 9 | yes | Butyl-terminated polyalkylene glycol wherein ethylene oxide and propylene oxide units are randomly distributed wherein the fraction of propylene oxide units relative to the total amount of alkylene oxide units is in the range of from 40 to 60% and the total number of alkylene-oxide groups is between 100 and 150 |
| Additive 10 | yes | block copolymer having a central polypropylene glycol block (molar mass = 1750 g/mol) flanked by two polyethylene glycol blocks wherein the percentage of said polyethylene glycol blocks of the molar mass of the molecule is 40%. |
| Additive 11 | yes | block copolymer having a central polypropylene glycol block (molar mass = 1750 g/mol) flanked by two polyethylene glycol blocks wherein the percentage of said polyethylene glycol blocks of the molar mass of the molecule is 80%. |

The invention claimed is:

1. A method for processing cellulose-containing biomass, comprising:

subjecting a treatment mixture comprising a cellulose-containing biomass, water, sulfuric acid, and at least one compound of formula (I) to a temperature in a range of from 100° C. to 220° C. at a pressure in a range of from 100 to 4000 kPa, wherein the pressure is selected such that at least a part of the water is in the liquid state, to generate a treated cellulose-containing biomass,

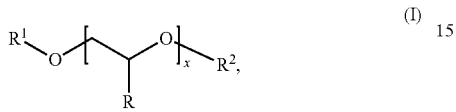

in the formula (I) each x group is formula (II), $R^1$ and $R^2$ are independently selected from the group consisting of hydrogen, methyl, ethyl, propyl and butyl, R in the formula (II) is independently selected from the group consisting of hydrogen, methyl, ethyl and propyl,

and x is an integer of from 50 to 250.

2. The method according to claim 1, wherein a concentration of the sulfuric acid in the treatment mixture is in a range of from 0.1 wt.-% to 25 wt.-%, based on the total weight of the cellulose-containing biomass present in the treatment mixture.

3. The method according to claim 1, wherein in the treatment mixture, an amount of methanesulfonic acid is less than 100 wt.-%, based on the weight of the sulfuric acid present in the treatment mixture.

4. The method according to claim 1, wherein in the at least one compound of formula (I), $R^1$ is hydrogen, $R^2$ is selected from the group consisting of hydrogen, methyl, propyl and butyl, and x is an integer of from 50 to 210.

5. The method according to claim 1, wherein (a) in one or more of the at least one compound of formula (I), $R^1$ and $R^2$ are selected from the group consisting of hydrogen and methyl, each R is hydrogen, and x is an integer of from 70 to 210, or (b) in one or more of the at least one compound of formula (I), $R^1$ is hydrogen or methyl, $R^2$ is selected from the group consisting of methyl, ethyl, propyl and butyl, and each R is either hydrogen or methyl, wherein R =hydrogen and R =methyl are randomly distributed, wherein in each molecule of the compound of formula (I) the fraction of groups (II) wherein R is methyl relative to the total amount of groups (II) is in a range of from 40 to 60%, and x is an integer of from 70 to 210, or (c) one or more of the at least one compound of formula (I) is a compound of formula (I')

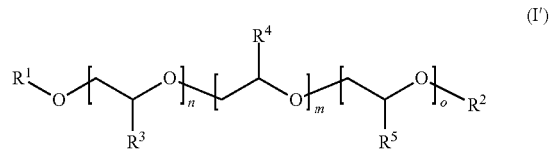

wherein $R^1$ and $R^2$ are hydrogen or methyl $R^3$, $R^4$ and $R^5$ are independently selected from the group consisting of hydrogen, methyl, ethyl and propyl with the proviso that all n $R^3$ are identical, all m $R^4$ are identical, and all o $R^5$ are identical, and $R^4$ is not identical to $R^3$, and $R^4$ is not identical to $R^5$, and n, m, o independently of each other are integers ≥1 with the proviso that the sum of m, n and o is from 50 to 210.

6. The method according to claim 1, wherein the cellulose-containing biomass is selected from the group consisting of plant biomass, an agricultural waste, a forestry residue, a sugar processing residue, paper waste, and a mixture thereof.

7. The method according to claim 1, wherein the temperature and the pressure are maintained for a duration of not more than 120 minutes.

8. The method according to claim 1, wherein the temperature is in a range of 110° C. to 180° C.

9. The method according to claim 1, wherein the pressure is in a range of from 100 kPa to 1600 kPa.

10. The method according to claim 1, wherein the treatment mixture comprises 3 wt.-% to 75 wt.-% of the cellulose-containing biomass, based on the total weight of the treatment mixture.

11. The method according to claim 1, wherein the treatment mixture is obtained by adding an aqueous treatment solution comprising the sulfuric acid and the at least one compound of formula (I) to the cellulose-containing biomass.

12. The method according to claim 11, wherein in the aqueous treatment solution, an amount of the sulfuric acid is in a range of from 0.1 wt.-% to 5.5 wt.-%, based on the total weight of the aqueous treatment solution, and/or a total amount of the at least one compound of formula (I) is in a range of from 0.01 wt.-% to 5 wt.-%, based on the total weight of the aqueous treatment solution.

13. The method according to claim 1, wherein in the treatment mixture, a total amount of the cellulose-containing biomass, the water, the sulfuric acid, and the at least one compound of formula (I) is at least 95 wt.-%, based on the total weight of the treatment mixture.

14. The method according to claim 1, further comprising:
saccharificating the treated cellulose-containing biomass such that at least one of glucose and another sugar is formed, and optionally fermenting and/or chemical processing the at least one of glucose and another sugar, or further processing the treated cellulose-containing biomass to obtain dissolving pulp.

15. The method according to claim 1, wherein a concentration of the sulfuric acid in the treatment mixture is in a range of from 1 wt.-% to 5 wt.-%, based on the total weight of the cellulose-containing biomass present in the treatment mixture.

16. The method according to claim 1, wherein the treatment mixture does not contain more than 1 wt.-% of methanesulfonic acid based on the weight of the sulfuric acid present in the treatment mixture.

17. The method according to claim 1, wherein the temperature is in a range of 120 ° C. to 175 ° C., and the pressure is in a range of from 100 kPa to 1000 kPa.

18. The method according to claim 1, wherein the treatment mixture comprises 30 wt.-% to 45 wt.-% of the cellulose-containing biomass, based on the total weight of the treatment mixture.

* * * * *

UNITED STATES PATENT AND TRADEMARK OFFICE
CERTIFICATE OF CORRECTION

PATENT NO. : 10,316,106 B2
APPLICATION NO. : 15/552521
DATED : June 11, 2019
INVENTOR(S) : Frank Rittig et al.

Page 1 of 1

It is certified that error appears in the above-identified patent and that said Letters Patent is hereby corrected as shown below:

In the Specification

Column 5, Line 49, "propy" should read --propyl--.

Signed and Sealed this
Twenty-eighth Day of January, 2020

Andrei Iancu
*Director of the United States Patent and Trademark Office*